US012564713B2

(12) United States Patent
Amaro et al.

(10) Patent No.: US 12,564,713 B2
(45) Date of Patent: Mar. 3, 2026

(54) ASSEMBLY OF AN IMPLANTING ACCESSORY AND A FLEXIBLE IMPLANTABLE STIMULATION LEAD

(71) Applicant: SORIN CRM SAS, Clamart (FR)

(72) Inventors: Diego Amaro, Le Plessis-Robinson (FR); Jean-François Ollivier, Gif-sur-Yvette (FR)

(73) Assignee: SORIN CRM SAS, Clamart (FR)

( * ) Notice: Subject to any disclaimer, the term of this patent is extended or adjusted under 35 U.S.C. 154(b) by 318 days.

(21) Appl. No.: 18/031,310

(22) PCT Filed: Oct. 15, 2021

(86) PCT No.: PCT/EP2021/078641
§ 371 (c)(1),
(2) Date: Apr. 11, 2023

(87) PCT Pub. No.: WO2022/079257
PCT Pub. Date: Apr. 21, 2022

(65) Prior Publication Data
US 2023/0372706 A1     Nov. 23, 2023

(30) Foreign Application Priority Data
Oct. 15, 2020     (FR) ...................................... 2010566

(51) Int. Cl.
A61N 1/05          (2006.01)
(52) U.S. Cl.
CPC .................................. A61N 1/0573 (2013.01)
(58) Field of Classification Search
CPC .... A61N 1/0573; A61N 1/057; A61N 1/3756;
A61N 1/056; A61N 1/37205;
(Continued)

(56) References Cited

U.S. PATENT DOCUMENTS 5,300,107 A * 4/1994 Stokes ................... A61N 1/057
607/126
6,321,123 B1 * 11/2001 Morris ................... A61N 1/056
600/374
(Continued)

FOREIGN PATENT DOCUMENTS

EP        0 784 993 A1       7/1997
EP        0 819 445 A1       1/1998
JP        2008534158        8/2008

OTHER PUBLICATIONS

International Search Report and Written Opinion on PCT Appl. Ser. No. PCT/EP2021/078641 dated Jan. 5, 2022 (21 pages).

*Primary Examiner* — Carl H Layno
*Assistant Examiner* — Anh-Khoa N Dinh

(57)     ABSTRACT

An assembly comprising an implanting accessory, and a stimulation lead. The lead configured to be combined with an active implantable medical device and implanted through a right ventricular free wall. The implanting accessory comprising a needle with a free puncturing end, where at least a first portion of the lead is configured to be inserted into an inner lumen of the needle. In a state where the first portion of the lead is inserted into the inner lumen, the first portion of the lead comprises at least a first branch that extends from the lead in a direction oriented toward the free puncturing end, the first branch extending from the lead from a junction point arranged a predetermined distance from a distal end of the lead, the predetermined distance corresponding to a second portion of the lead between the junction point and the distal end of the lead.

19 Claims, 4 Drawing Sheets

(58) Field of Classification Search
CPC .......... A61N 1/37518; A61N 2001/058; A61N
2001/0578; A61N 1/37512; A61N
2001/0585; A61N 1/0504; A61N 1/059;
A61N 1/05; A61N 1/0587; A61N 1/3918;
A61N 1/3968; A61N 1/0563; A61N
1/0565; A61N 1/0568; A61N 1/3627;
A61N 1/368
See application file for complete search history.

(56) References Cited

U.S. PATENT DOCUMENTS

| | | | |
|---|---|---|---|
| 7,321,798 | B2 | 1/2008 | Muhlenberg et al. |
| 2004/0215307 | A1* | 10/2004 | Michels ................. A61N 1/057 |
| | | | 607/126 |
| 2005/0136385 | A1* | 6/2005 | Mann .................... A61N 1/025 |
| | | | 434/320 |
| 2006/0041300 | A1* | 2/2006 | Zhang ................... A61N 1/057 |
| | | | 607/126 |
| 2012/0130464 | A1* | 5/2012 | Ollivier ............... A61N 1/0587 |
| | | | 607/122 |
| 2014/0107756 | A1 | 4/2014 | Ollivier |
| 2015/0157268 | A1* | 6/2015 | Winshtein ........... A61B 5/6882 |
| | | | 600/300 |
| 2015/0320330 | A1 | 11/2015 | Sparks et al. |
| 2019/0038893 | A1 | 2/2019 | Garai et al. |

* cited by examiner

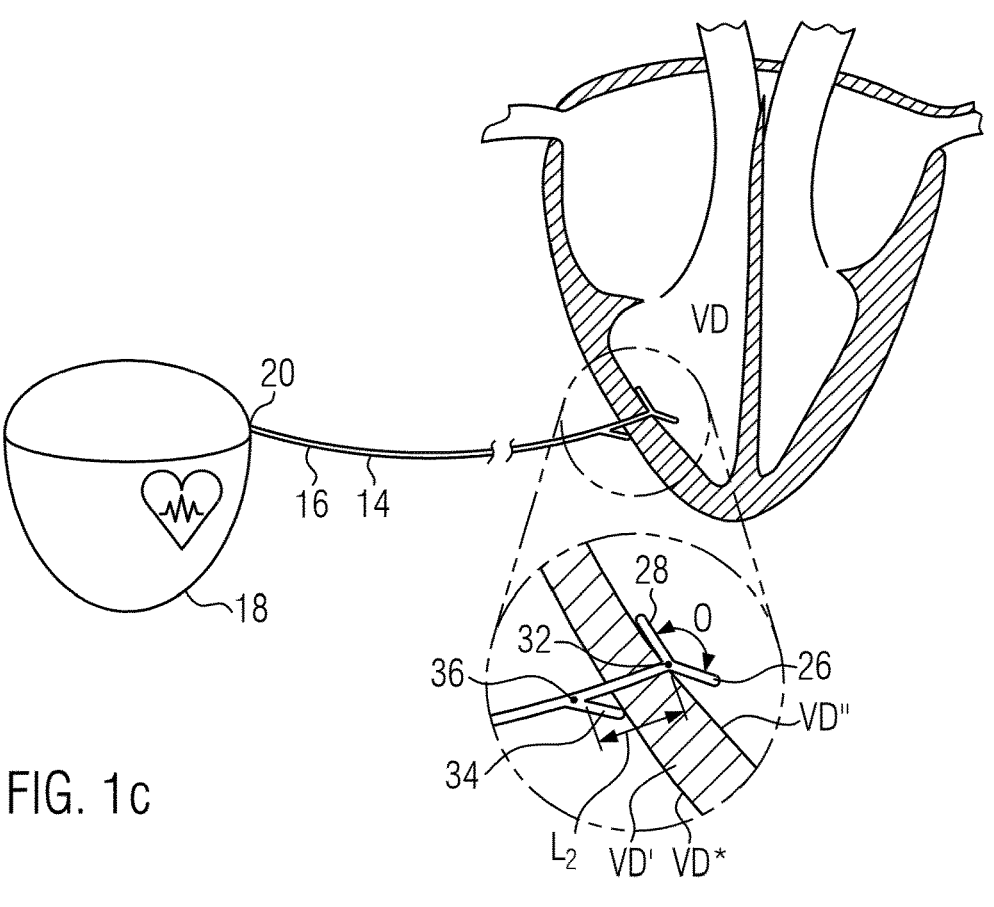
FIG. 1c
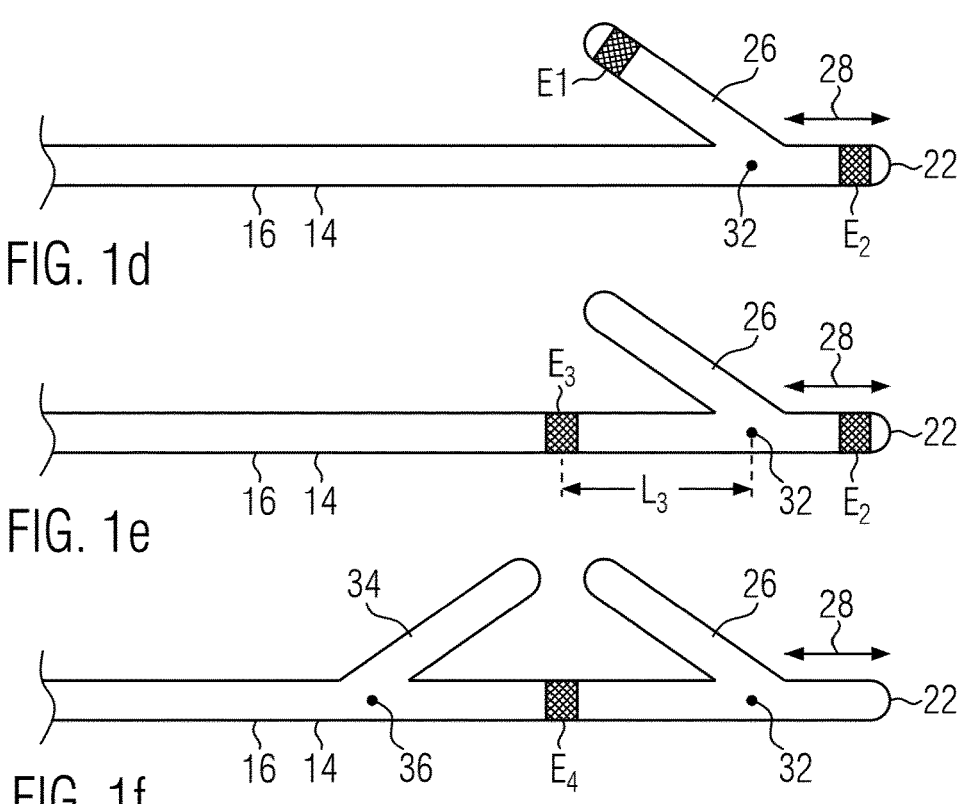
FIG. 1d
FIG. 1e
FIG. 1f

1

ASSEMBLY OF AN IMPLANTING ACCESSORY AND A FLEXIBLE IMPLANTABLE STIMULATION LEAD

CROSS-REFERENCE TO RELATED PATENT APPLICATIONS

This application is a National Stage filing of International Application No. PCT/EP2021/078641, filed on Oct. 15, 2021, which claims the benefit of and priority to French Patent Application No. 2010566, filed on Oct. 15, 2020, the entire disclosure of which is hereby incorporated by reference herein.

TECHNICAL FIELD

The present invention relates to an assembly of an implanting accessory and a flexible implantable stimulation lead for an active implantable medical device.

The present invention also relates to a method for implanting such a lead through a heart wall, in particular through the right ventricular free wall.

BACKGROUND

It is known to stimulate the right ventricle by housing a so-called endocardial lead in the right ventricle of the heart, where it is inserted via the venous network, or using a so-called endocavitary lead implanted in the cavities by venous access.

It is also known to use so-called epicardial leads that are attached directly on the outer wall of the myocardium. However, an epicardial lead often yields poorer results than those obtained with an endocardial lead, in particular in terms of electrical performance.

Furthermore, it is known to maintain the epicardial leads to the wall of the epicardium by suturing or screwing a helical anchoring screw of the lead, but these mechanical fastenings have the drawback of being invasive and relatively traumatic for the tissue.

Thus, the biggest drawback of the known epicardial leads is the invasive aspect of the procedure relative to the endocavitary leads.

Furthermore, aside from the invasive nature of their implantation, another drawback common to these known epicardial leads lies in their low electrical performance, which is detrimental to the effectiveness of the stimulation.

SUMMARY

The invention seeks to overcome the various limitations set out above by proposing a stimulation lead allowing improved effectiveness of the stimulation while reducing the invasiveness of its implantation.

The aim of the present invention is achieved using an assembly of an implanting accessory and a flexible implantable stimulation lead. Said lead comprises a lead body, and is able to be combined with an active implantable medical device via its proximal end and is configured to be implanted through a heart wall, in particular through the right ventricular free wall, via its distal end. The implanting accessory comprises a needle with a pointed free puncturing end, at least the distal part of the needle being a hollow needle comprising an inner lumen opening onto the pointed free puncturing end, at least a first portion of the lead being able to be inserted via its distal end into the inner lumen of the needle. In a state where the first portion of the lead is inserted into the lumen of the needle, said first portion of the lead comprises at least a first branch that extends from the lead body in a direction oriented toward the pointed free end of the needle, the first branch extending from the lead body from a junction point arranged at a predetermined distance from the distal end that forms a second portion of the lead body between the junction point of the first branch and the distal end of the lead.

Thus, the needle makes it possible to puncture the right ventricular wall of the heart and to introduce the lead therein. Since the lead comprises, at its distal end, a first branch and a second portion of the lead body, said lead is thus provided with a retaining means when the lead is implanted through the free wall of the right ventricle. This retaining means of the lead is able to be inserted into the needle, by means of which it can be implanted in the heart tissue.

Since the lead is implantable through the right ventricular free wall, the first branch and the second portion of the lead body can be arranged in the right ventricle, in particular against the inner wall.

The present invention, which relates to an assembly of an implanting accessory and a flexible implantable stimulation lead, may be further improved through the following embodiments.

According to one embodiment, the lead body may further comprise a third portion that is less rigid than said first branch and the second portion, the third portion extending toward the proximal end of the lead from the junction point of the first branch, such that the first branch and the second portion are configured to pivot securely with one another relative to said junction point.

Thus, the first branch and the second portion are secured to one another during a pivoting movement about the junction point. This pivoting makes it possible to arrange the retaining means of the lead against the right ventricular inner wall in an implanted state of the lead.

According to one embodiment, in a state where the first portion of the lead is inserted into the lumen of the needle, the first branch and the second portion can form an obtuse angle and the first branch and the third portion can form an acute angle.

Thus, the first branch is arranged so as to be able to provide a retaining means in an implanted state of the lead after the first branch and the second branch pivot securely with one another relative to the junction point.

According to one embodiment, the first branch and/or the second portion may comprise at least one electrode.

Thus, in an implanted state of the lead, the at least one electrode, in particular the anode, may be arranged on the inner wall of the right ventricle. As a result, owing to the direct contact of the anode with the heart wall, the stimulation may be improved.

According to one embodiment, the lead body may comprise at least one electrode that is spaced away from the junction point of the lead by a length of between 2 and 50 mm, in particular between 2 and 30 mm.

Thus, these dimensions make it possible, in an implanted state of the lead, to arrange the at least one electrode, in particular the cathode, in the thickness of the heart wall, in particular of the right ventricular free wall. Thus, the stimulation and the detection are improved that much more. Stimulation is also made possible at lower energies than when the electrodes are not in direct contact with the heart wall.

According to one embodiment, the first branch and the second portion may each have a length of between 2 and 20 mm.

These dimensions make it possible to improve the contact surface of the retaining means against the right ventricular inner wall and thus to increase the retention of the lead through the right ventricular inner wall, while allowing simple and damage-free removal of the device by sustained traction.

According to one embodiment, the lead body may comprise a zone that is reinforced and elastic relative to the rest of the lead body, said zone being different from the first portion and corresponding to a bending zone of the lead.

Thus, the robustness and therefore the lifetime of the lead can be increased despite the bending of the lead in this location.

Furthermore, the elasticity of this bending zone allows an automatic elastic deployment, which is therefore simple to implement, once the first portion of the lead is moved out of the lumen of the needle and it is no longer retained against the inner wall of the lumen of the needle.

According to one embodiment, the first portion of the lead may further comprise a bearing means formed by a second branch that extends from the lead body in a direction oriented toward the distal end of the lead, the second branch extending from the lead body from a junction point of the lead body that is different from said second portion and the first branch.

The bearing means makes it possible to improve the maintenance of the lead to the heart wall by preventing unwanted migration of the lead into the ventricle after implantation of said lead. The bearing means in fact bears against the right ventricular outer free wall in the implanted state of said lead.

According to one embodiment, the junction point of the second branch with the lead body may be spaced apart by a distance of between 1 and 30 mm from the junction point of the first branch.

These dimensions substantially correspond to the thickness of the heart wall at the right ventricle. Thus, the lead is structurally configured so that the first branch and the second branch protrude from the lead body on either side of the right ventricular free wall in an implanted state of the lead, each of the branches making it possible to retain the lead to the heart muscle.

According to one embodiment, the lead body may comprise at least one electrode arranged between the junction point of the first branch and the junction point of the second branch.

Thus, the at least one electrode may advantageously be arranged in the thickness of the right ventricular free wall, which improves the stimulation of the right ventricle.

According to one embodiment, the lead may be a flexible microwire comprising an electrically conductive core coated with an electrically insulating layer, and the at least one electrode being formed by a stripped zone of the microwire and the diameter of the microwire being no more than 1 French (0.33 mm).

Thus, owing to the dimensions of the microwire, it is possible to make the implantation of the lead less invasive. In fact, the puncture through the heart tissue to introduce the microwire may be reduced to a diameter of about 1 French. As a result, it becomes possible to cause less damage to the tissue during the implantation and removal of the lead.

The aim of the invention is also achieved by means of a flexible implantable stimulation lead for an assembly as described above. Said lead comprises a lead body. Said lead is able to be combined with an active implantable medical device via its proximal end and configured to be implanted through a heart wall, in particular through the right ventricular free wall, via its distal end. Said lead comprises a first portion configured to be inserted into a needle. The first portion comprises at least a first branch that extends from the lead body in a direction oriented toward the proximal end of the lead and toward the pointed free end of the needle when the first portion is inserted into the needle, the first branch extending from the lead body at a predetermined distance from the distal end that forms a second portion of the lead body between the first branch and the distal end of the lead.

Because the lead comprises, at its distal end, a first branch and a second portion of the lead body, said lead is thus provided with a retaining means when the lead is implanted through the right ventricular free wall. This retaining means of the lead is able to be inserted into the needle, by means of which it can be implanted into the heart tissue.

Since the lead is able to be implanted through the right ventricular free wall, such that the first branch and the second portion of the lead body are arranged in the right ventricle against the inner wall, the contact zones between the lead and the wall of the myocardium are increased, which allows improved electrical performance of the lead.

According to one embodiment, the first portion of the lead may further comprise a bearing means formed by a second branch that extends from the lead body in a direction oriented toward the distal end of the lead, the second branch extending from the lead body from a junction point of the lead body that is different both from said second portion and from the first branch.

The bearing means allows improved maintenance of the lead to the heart wall by preventing unwanted migration of the lead into the ventricle after implantation of said lead. The bearing means in fact bears against the right ventricular outer free wall in the implanted state of said lead.

DESCRIPTION OF THE FIGURES

The invention and its advantages will be explained in more detail hereinafter using preferred embodiments and based in particular on the following figures, in which:

FIG. 1c shows a schematic view of the flexible implantable stimulation lead illustrated in FIG. 1a and FIG. 1b in an implanted state of the lead.

FIG. 1d shows a partial and schematic view of the flexible implantable stimulation lead illustrated in FIG. 1a to FIG. 1c according to a first variant.

FIG. 1e shows a partial and schematic view of the flexible implantable stimulation lead illustrated in FIG. 1a to FIG. 1c according to a second variant.

FIG. 1f shows a partial and schematic view of the flexible implantable stimulation lead illustrated in FIG. 1a to FIG. 1c according to a third variant.

5

Figures 2A, 2B, 2C, 2D, 2E:
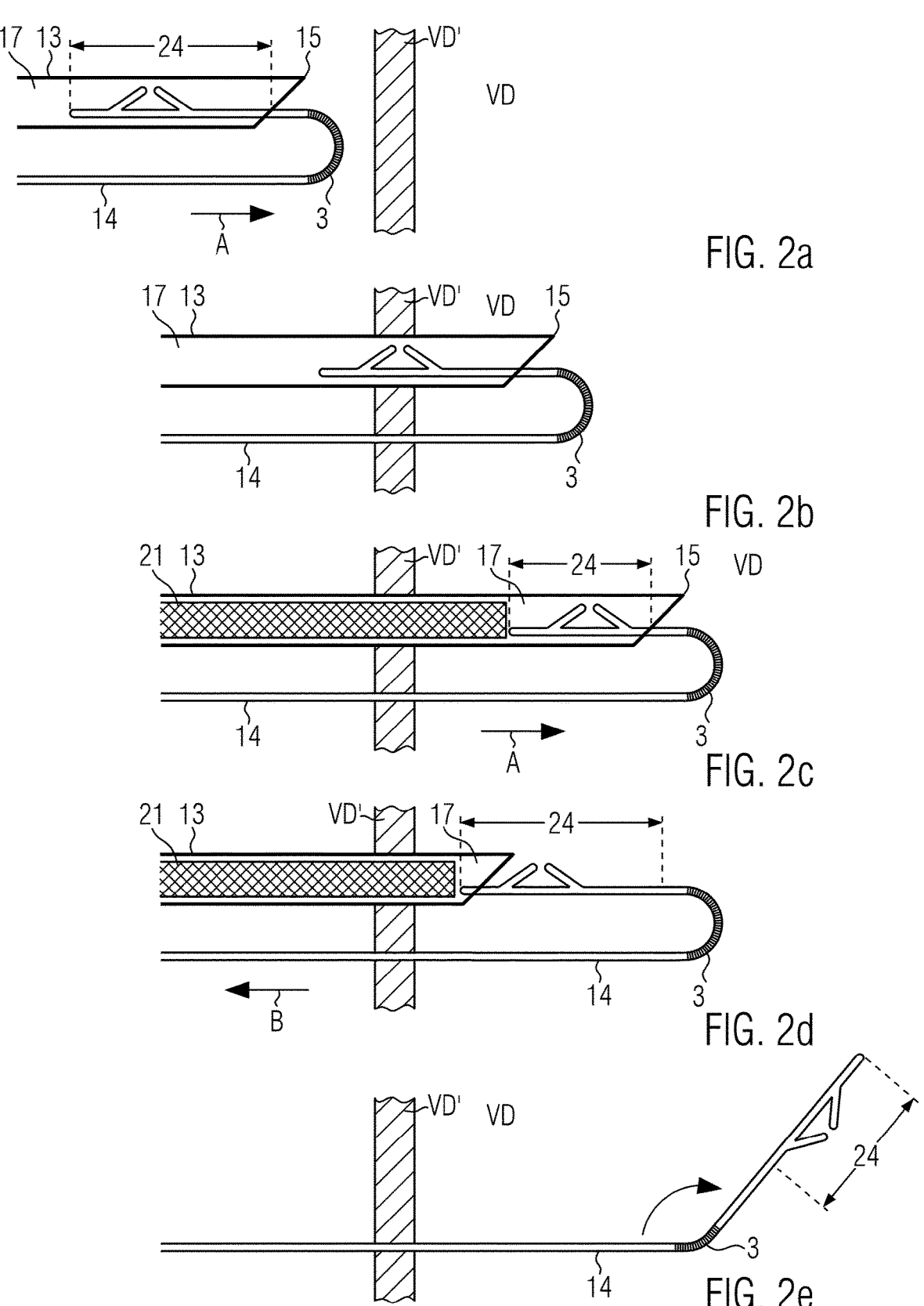
FIG. 2a shows a schematic view of a step of implanting the lead according to the present invention.
FIG. 2b shows a schematic view of a step of implanting the lead according to the present invention.
FIG. 2c shows a schematic view of a step of implanting the lead according to the present invention.

FIG. 2d shows a schematic view of a step of implanting the lead according to the present invention.

FIG. 2e shows a schematic view of a step of implanting the lead according to the present invention.

Figures 2F, 2G, 2H, 2I, 2J, 2K:
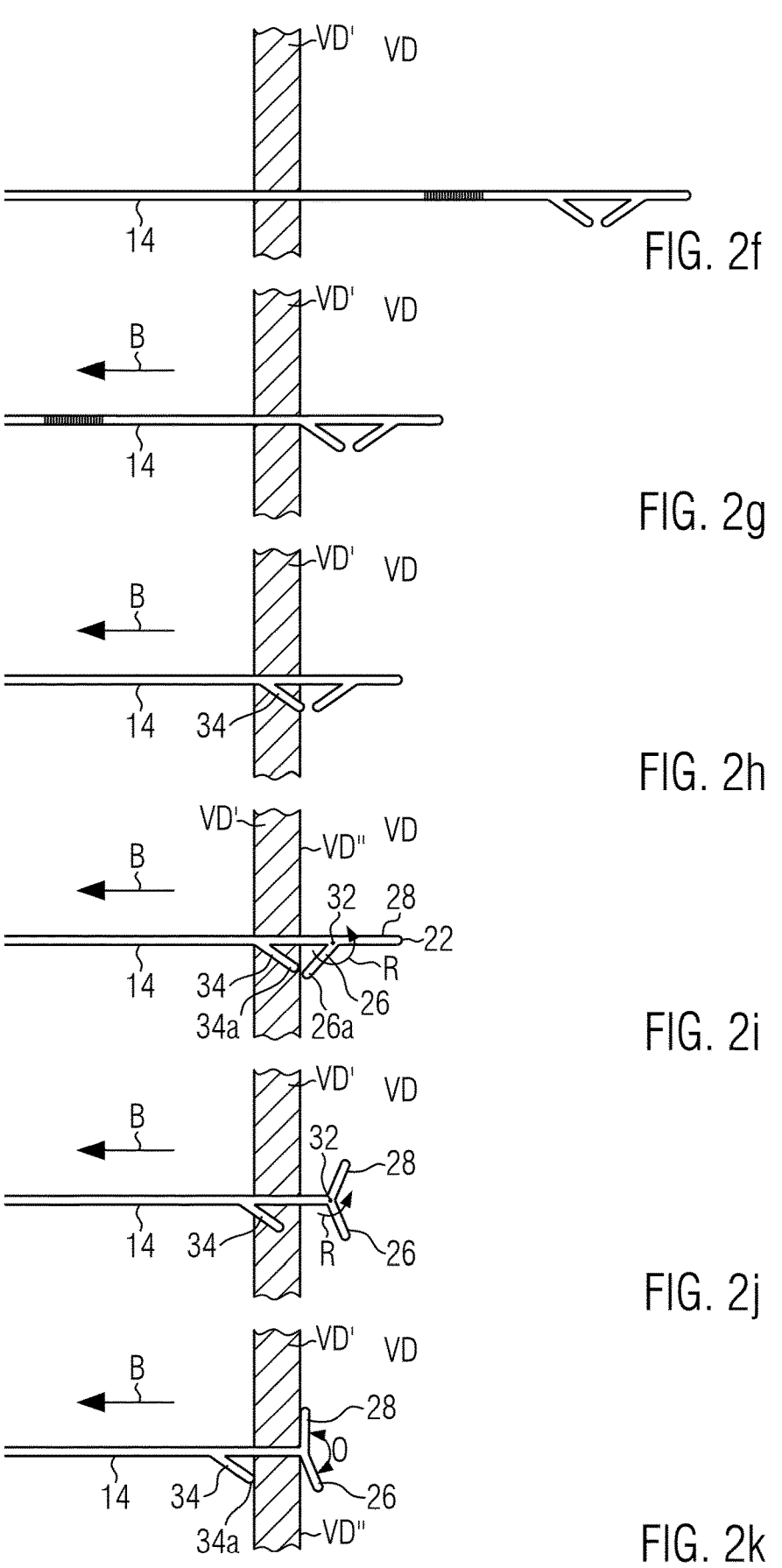

FIG. 2f shows a schematic view of a step of implanting the lead according to the present invention.

FIG. 2g shows a schematic view of a step of implanting the lead according to the present invention.

FIG. 2h shows a schematic view of a step of implanting the lead according to the present invention.

FIG. 2i shows a schematic view of a step of implanting the lead according to the present invention.

FIG. 2j shows a schematic view of a step of implanting the lead according to the present invention.

FIG. 2k shows a schematic view of a step of implanting the lead according to the present invention.

DETAILED DESCRIPTION

Figures 1A, 1B:
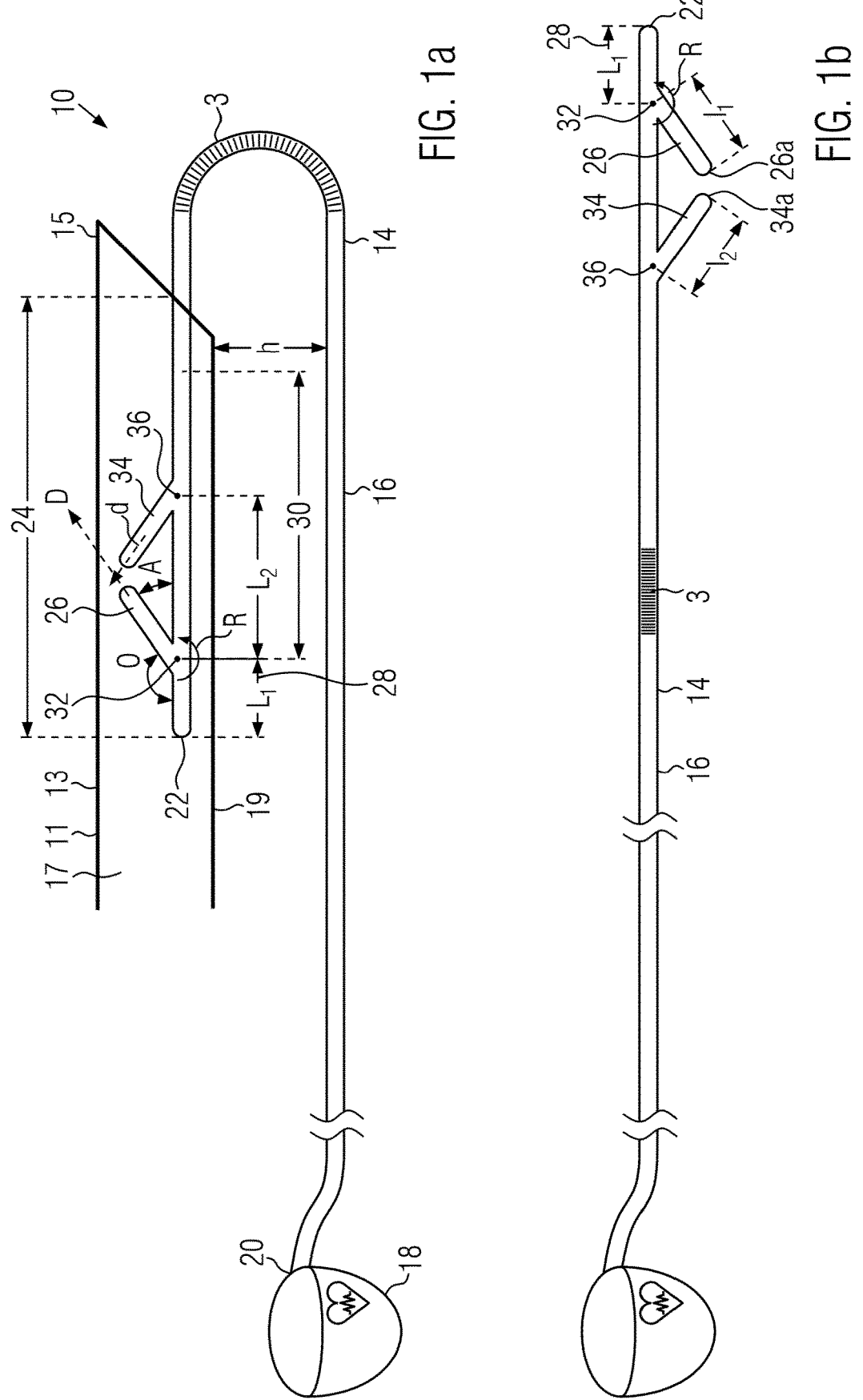
FIG. 1a shows a partial and schematic view of the assembly of an implanting accessory and a flexible implantable stimulation lead according to the present invention in a non-implanted state of the lead.
FIG. 1b shows a partial and schematic view of the flexible implantable stimulation lead illustrated in FIG. 1a in a non-implanted state of the lead.

FIG. 1a shows a partial and schematic view of the assembly 10 of an implanting accessory 11 and a flexible implantable stimulation lead 14 according to the present invention in a non-implanted state of the lead. For clarity reasons, hereinafter, the elements related to the implanting accessory 11 are described using odd-numbered reference numerals, while the elements related to the lead 14 are described using even-numbered reference numerals.

Since FIG. 1b shows a partial and schematic view of the flexible implantable stimulation lead 14 illustrated in FIG. 1a in a non-implanted state of the lead, FIG. 1a and FIG. 1b are described jointly hereinafter.

The lead 14 comprises a lead body 16.

The lead 14 is able to be combined with an active implantable medical device 18 via the proximal end 20 of the lead 14.

The lead 14 is configured to be implanted via the distal end 22 of the lead 14 through a heart wall, in particular through the right ventricular free wall. The distal end 22 is opposite the proximal end 20 of the lead 14.

FIG. 1c illustrates a schematic view of the flexible implantable stimulation lead 14 in an implanted state of the lead.

The elements with the same reference numerals used to describe FIG. 1a, FIG. 1b and FIG. 1c relate to the same elements and will not be described again in detail for each of FIG. 1a, FIG. 1b and FIG. 1c.

FIG. 1a illustrates a partial view of a needle 13 comprised in the implanting accessory 11 according to the present invention.

The needle 13 is provided with a pointed free puncturing end 15. The pointed free puncturing end 15 corresponds to the distal end of the needle 13.

The needle 13, at least in its distal part, that is to say, at least the part of the needle 13 that is illustrated in FIG. 1a, is a hollow needle comprising an inner lumen 17 opening onto the pointed free puncturing end 15.

The implanting accessory 11 according to the present invention also comprises a plunger means able to be housed and to slide in the lumen 17 of the needle 13 (this plunger means is not shown in FIG. 1a to FIG. 1c). This plunger means is visible in FIG. 2c and FIG. 2d, which will be described hereinafter in more detail.

According to the present invention, a first portion 24 of the lead 14 is able to be inserted via its distal end 22 into the inner lumen 17 of the needle 13.

FIG. 1a illustrates a state of the lead 14 in which the first portion 24 of the lead 14 is inserted into the lumen 17 of the needle 13.

It should be noted that the height h illustrated in FIG. 1a between the needle 13 and the lead body 16 that is not inserted into the lumen 17 of the needle 13 is shown as being non-zero only for reasons related to the clarity of the illustration. One skilled in the art must understand that to implement the present invention, in the state where the first portion 24 of the lead 14 is inserted into the lumen 17 of the needle 13, the rest of the lead body 16 extends along the outer wall 19 of the needle 13, such that contact is possible, but not necessary, between the lead body 16 and the outer wall 19 of the needle 13.

The first portion 24 of the lead 14 comprises at least a first branch 26 that extends from the lead body 16 in a direction D oriented toward the pointed free end 15 of the needle.

The first branch 26 extends from the lead body 16 at a predetermined distance L1 from the distal end 22 of the lead 14. The portion of the lead body 16 of length L1 from the distal end 22 forms a second portion 28 of the lead body 16 arranged between the first branch 26 and the distal end 22 of the lead 14.

As illustrated in FIG. 1c, the first branch 26 and the second portion 28 of the lead 14 serve as retaining means to maintain the lead 14 through a free wall VD' of the right ventricle VD. In the implanted state of the lead 14 shown in FIG. 1c, the first branch 26 and the second portion 28 of the lead 14 are arranged so as to extend longitudinally along the inner wall VD" of the right ventricle VD.

As illustrated in FIG. 1b, the first branch 26 has a length l1 between a junction point 32 of the lead body 16 of the first branch 26 and the free end 26a of the first branch. The length l1 is between 2 and 20 mm.

The length L1 of the second portion 28 and the length l1 of the first branch 26 may be substantially equal to one another.

These dimensions make it possible to improve the contact surface of the retaining means against the inner wall VD" of the right ventricle VD and thus to further increase the retention of the lead 14 through the inner wall VD' of the right ventricle VD". Furthermore, the rigidity of the retaining means in the immediate vicinity of the junction point 32 makes it possible to generate the retention.

In an embodiment of the present invention like the one illustrated in FIG. 1a to FIG. 1c, the lead body 16 may further comprise a third portion 30 that is less rigid than the first branch 26 and the second portion 28. The third portion 30 extends toward the proximal end 20 of the lead 14, that is to say, toward the pointed free end 15 of the needle in the illustration of FIG. 1a. The third portion 30 extends from a junction point 32 of the lead body 16 between the first branch 26 and the second portion 28, such that the first branch 26 and the second portion 28 are configured to pivot (annotated by reference R in FIG. 1a and FIG. 1b) securely with respect to one another relative to the junction point 32 of the lead body 16. The length of the third portion 30 may be adapted based on the thickness of the heart muscle of the targeted region.

Thus, the first branch 26 and the second portion 28 are secured to one another during a pivoting movement R about the junction point 32. This pivoting R makes it possible to arrange the retaining means of the lead 14 against the inner wall VD" of the right ventricle VD in an implanted state of the lead 14, as illustrated in FIG. 1c.

As illustrated in FIG. 1a, which shows a state where the first portion 24 of the lead 14 is inserted into the lumen 17 of the needle 13, the first branch 26 and the second portion 28 form an obtuse angle O while the first branch 26 and the third portion 30 form an acute angle A. An obtuse angle is an angle whose measurement in degrees is between 90° and 180°. In particular, the obtuse angle O formed between the first branch 26 and the second portion 28 has a measurement in degrees of about 135°.

As described above, since the first branch 26 and the second portion 28 of the lead 14 are configured to pivot securely with respect to one another relative to the junction point 32 of the lead body 16, the obtuse angle O between the first branch 26 and the second portion 28 of the lead 14 is maintained in the implanted state of the lead 14, as illustrated in FIG. 1c.

The obtuse angle O between the first branch 26 and the second portion 28 of the lead 14 makes it possible to arrange the first branch 26 and the second portion 28 along the inner wall VD" of the right ventricle VD and thus to provide a retaining means for the lead 14.

In an embodiment of the present invention like the one illustrated in FIG. 1a to FIG. 1c, the first portion 26 of the lead 14 may further comprise a bearing means formed by a second branch 34 that extends from the lead body 16 in a direction d oriented toward the distal end 22 of the lead 14. The second branch 34 extends from the lead body 16 from a junction point 36. The junction point 36 is comprised in a portion of the lead body 16 that is different both from the second portion 28 and from the first branch 26.

In the embodiment illustrated in FIG. 1a, the junction point 36 is comprised in the third portion 30 of the lead 14. In a variant, the junction point 36 is located on the lead body 16 past the third portion 30.

The second branch 34 of the lead 14 provides a bearing means that makes it possible to improve the maintenance of the lead 14 to the wall VD' of the right ventricle VD while preventing unwanted migration of the lead 14 into the right ventricle VD after implantation of the lead 14 (see FIG. 1c). The bearing means 34 in fact bears against the outer free wall VD* of the right ventricle VD in the implanted state of the lead 14, as illustrated in FIG. 1c.

As illustrated in FIG. 1b, the second branch 34 has a length 12 between a junction point 36 of the lead body 16 of the second branch 34 and the free end 34a of the second branch 34. The length 12 is between 2 and 20 mm.

The length 11 of the first branch 26 and the length 12 of the second branch 34 may be substantially equal to one another.

The junction point 36 of the second branch 34 with the lead body 14 is spaced apart by a length L2 of between 1 and 30 mm from the junction point 32 of the first branch 26.

These dimensions substantially correspond to the thickness of the heart wall VD' at the right ventricle VD. Thus, the lead 14 is structurally configured so that the first branch 26 and the second branch 34 protrude from the lead body 16 on either side of the wall VD' of the right ventricle VD in the implanted state of the lead 14, each of the branches 26, 34 making it possible to retain the lead 14 to the heart muscle.

Since the lead 14 is a stimulation lead, it comprises at least one stimulation electrode.

In a variant, the lead 14 may also comprise at least one detection electrode.

FIG. 1d to FIG. 1f illustrate variant embodiments of the first portion 24 of the lead 14 comprising at least one electrode. These variants may be combined with one another. The present invention is not limited to the variants illustrated in FIG. 1d to FIG. 1f.

The elements with the same reference numerals that have already been used to describe FIG. 1a to FIG. 1c will not be described again in detail, and reference is made to their descriptions above.

FIG. 1d illustrates a first portion 24 that comprises only one branch 26. In this variant, the first branch 26 and the distal end 22 of the second portion 28 each comprise an electrode E1, E2. Like in FIG. 1d, FIG. 1e illustrates a first portion 24 that comprises only one branch 26. In this variant, the distal end 22 of the second portion 28 comprises an electrode E2 and the lead body 16 further comprises an electrode E3 spaced apart by a length L3 from the junction point 32 of the lead 14. The length L3 is between 2 and 50 mm, in particular between 2 and 30 mm.

The electrode E3 may be a cathode E3 that is preferably located on the proximal side of the junction point 32 of the lead 14 so as to position the cathode E3 in the thickness of the heart muscle. Thus, the cathode E3 is in contact with the right ventricular wall in the thickness of the wall VD' rather than on the surface of the inner wall VD".

The length L3 is thus defined as the distance between the junction point 32 and the electrode E3, so as to maintain the cathode E3 in the heart muscle, i.e., in the thickness of the wall VD'. In fact, since surface contact is more subject to micro-movements due to the heartbeat, it is preferable to position the cathode E3 in the thickness of the wall of the right ventricle VD'.

Thus, these dimensions make it possible, in an implanted state of the lead, to arrange the electrode E3 in the thickness of the heart wall, in particular of the right ventricular free wall. As a result, the stimulation is further improved.

FIG. 1f illustrates a first portion 24 that comprises a first branch 26 and a second branch 34. In this variant, the lead body 16 comprises an electrode E4 arranged between the junction point 32 of the first branch 26 and the junction point 36 of the second branch 34.

Thus, the electrode E4 may advantageously be arranged in the thickness of the right ventricular free wall, which improves the stimulation of the right ventricle.

In a variant, the retaining function of the second branch 34 may be obtained via an elastic conformation along a curve radius (3 to 30 mm in radius) of the lead body 16 beginning at the electrode E4. The advantages of this variant lie in the fact that there is a lower impact on the pericardial sac and the lead body 16 is oriented tangentially to the outer wall of the muscle, which configuration puts less stress on the lead body 16 (mechanical fatigue resistance). This curve may replace or complement the retaining function of the second branch 34.

In another variant, the lead 14 may be provided with four electrically independent electrodes so as to optimize the stimulation/detection system for a given implantation zone.

Since the stimulation electrodes are in direct contact with the heart wall, stimulation at lower energies is also made possible.

The present invention also makes it possible to avoid needing to introduce a lead into the right ventricular cavity to stimulate the right ventricle. The implantation of the lead is thus made less invasive. The vasculature of the patient receiving the implant is thus not altered.

Furthermore, according to one embodiment, the lead may be a flexible microwire comprising an electrically conductive core coated with an electrically insulating layer, and the at least one electrode may be formed by a stripped zone of the microwire. In this embodiment, the diameter of the microwire is at most 1 French (0.33 mm).

Thus, owing to the dimensions of the microwire, it becomes possible to make the implantation of the lead even less invasive.

The overwhelming advantage of this technique in fact lies in the micro-invasive aspect. In view of the very small diameter of the lead, it is possible to use gauge 18 to gauge 24 puncture needles allowing placement by subxiphoid puncture (without needing to make a surgical opening requiring closing means, such as one or more sutures). Beyond the quicker patient recovery, this approach has the advantage of decreased risks of infection.

Furthermore, the lead body 16 according to the present invention may comprise a zone 3 that is reinforced and elastic relative to the rest of the lead body 16. This zone 3 is different from the first portion 24 and corresponds to a bending zone of the lead 14, as illustrated in FIG. 1a. Thus, the robustness and therefore the lifetime of the lead 14 may be increased despite the bending of the lead in this zone 3.

The implantation of the lead 14 is further described in reference to the description of the method for implanting such a lead through a heart wall, in particular through the right ventricular free wall, by means of FIG. 2a to FIG. 2k.

The elements with the same reference numerals that have already been used to describe FIG. 1a to FIG. 1c will not be described again in detail, and reference is made to the descriptions above.

In the first step of the implanting method according to the present invention as illustrated in FIG. 2a, a first portion 24 of the lead 14 is inserted into the lumen 17 of the needle 13. The lead 14 is bent at the bending zone 3 like in FIG. 1a previously described.

The needle 13 performs the puncture from the thoracic surface, then is brought closer to the wall of the right ventricle VD' in direction A.

The needle 13 is moved until the free puncturing end 15 of the needle 13 punctures the wall of the right ventricle VD' as illustrated in FIG. 2b.

Many guiding/identification systems can be used: surface or transesophageal ultrasound, stimulation, anatomical surface identification, injection of contrast medium under image intensifier. This list is not exhaustive.

While the free puncturing end 15 of the needle 13 is located inside the right ventricle VD, a plunger means 21 of the implanting accessory according to the present invention pushes the first portion 24 of the lead 14 in direction A outside the lumen 17 of the needle 13, as illustrated in FIG. 2c.

FIG. 2d shows a following step in which the first portion 24 of the lead 14 is practically entirely outside the lumen 17 of the needle 13.

The plunger means 21 is then retracted in a direction B opposite direction A and the needle 13 is removed from the wall VD' in direction B.

Thus, in the step of FIG. 2e, the first portion 24 of the lead 14 is outside the needle 13 and is in the right ventricle VD. The flexibility and the elasticity of the bending zone 3 cause the deployment of the lead 14 until reaching the configuration illustrated in FIG. 2f, which also corresponds to the configuration of FIG. 2b previously described.

Next, as illustrated in FIG. 2g, then FIG. 2h, the lead 14 is pulled slightly in direction B. Direction B extends from the inside of the right ventricle toward the outside of the heart.

In the step of FIG. 2i, the second branch 34 slides through the wall of the right ventricle VD' toward the outside of the heart in direction B. The orientation of the second branch 24, the free end 34a of which points toward the distal end 22 of the lead 14, makes it possible to facilitate the removal movement in direction B of the second branch 24.

The free end 26a of the first branch 26 comes to abut against the inner wall VD" of the right ventricle VD. This abutment drives the pivoting R of the first branch 26 and the second portion 28 of the lead 14 relative to the junction point 32, as illustrated in FIG. 2i.

As illustrated in FIG. 2j, the pivoting R continues so as to pivot the first branch 26 and the second portion 28 of the lead 14 by about 90° relative to the initial position in the needle 13 as illustrated in FIG. 2a.

At the same time as the pivoting of the first branch 26 and the second portion 28, the lead 14 continues to be pulled in direction B until the first branch 26 and the second portion 28 of the lead 14 come to bear against the inner wall VD" of the right ventricle CD as illustrated in FIG. 2k, thus substantially limiting the pivoting to a 90° angle.

The obtuse angle O formed between the first branch 26 and the second portion 28 makes it possible to prevent an unwanted removal of the lead 14 in direction B by positioning the first branch 26 and the second portion 28 of the lead 14 bearing against the inner wall VD" of the right ventricle CD. In fact, when the lead 14 is pulled in sense and direction B, the first branch 26 and the second portion 28 of the lead 14 abut against the inner wall VD" of the right ventricle CD. This abutment prevents any unwanted removal of the lead 14 from the right ventricle.

The proper positioning of the lead 14 may be confirmed by the electrical performance, attesting to the proper positioning of the electrodes, or by an ultrasound check or under image intensification.

The second branch 34 serves as bearing means, the free end 34a of the second branch 24 abutting against the outer wall VD* of the heart.

The bearing means 34 makes it possible to improve the maintenance of the lead 14 to the heart wall VD by preventing unwanted migration of the lead 14 in direction A into the ventricle VD after implantation of said lead.

The invention claimed is:

1. An assembly comprising:
an implanting accessory; and
a flexible implantable stimulation lead,
the lead comprising a lead body, and
the lead being configured to be combined with an active implantable medical device via a proximal end of the lead, and the lead being configured to be implanted through a right ventricular free wall via a distal end of the lead,
the implanting accessory comprising a needle with a pointed free puncturing end, wherein at least a distal part of the needle is a hollow needle comprising an inner lumen opening onto the pointed free puncturing end,
wherein at least a first portion of the lead is configured to be inserted, via the distal end of the lead, into the inner lumen of the needle,
wherein in a state where the first portion of the lead is inserted into the inner lumen of the needle, the first portion of the lead comprises at least a first branch that extends from the lead body in a direction oriented toward the pointed free puncturing end of the needle, and
wherein the first branch extending from the lead body from a junction point is arranged in a predetermined distance from the distal end of the lead, the predetermined distance corresponding to a second portion of the lead body between the junction point of the first branch and the distal end of the lead;

wherein the lead body further comprises a third portion that is less rigid than the first branch and the second portion, the third portion extending toward the proximal end of the lead from the junction point of the first branch, such that the first branch and the second portion are configured to pivot securely with one another relative to the junction point of the first branch, wherein the first branch, the second portion, and the third portion are formed of the lead body as a single, continuous piece, the third portion defining a bending zone of the lead distinct from the first portion, about which the first branch and the second portion pivot securely relative to the junction point.

2. The assembly according to claim 1, wherein, in a state where the first portion of the lead is inserted into the inner lumen of the needle, the first branch and the second portion of the lead body form an obtuse angle and the first branch and the third portion form an acute angle.

3. The assembly according to claim 1, wherein the first branch and/or the second portion comprise at least one electrode.

4. The assembly according to claim 1, wherein the lead body comprises at least one electrode that is spaced away from the junction point of the lead by a length of between 2 and 50 mm.

5. The assembly according to claim 4, wherein the length is between 2 and 30 mm.

6. The assembly according to claim 1, wherein the first branch and the second portion each have a length of between 2 and 20 mm.

7. The assembly according to claim 1, wherein the lead body comprises a zone that is reinforced and elastic relative to the rest of the lead body.

8. The assembly according to claim 7, wherein the zone is different from the first portion and corresponding to a bending zone of the lead.

9. The assembly according to claim 1, wherein the first portion of the lead further comprises a bearing formed by a second branch that extends from the lead body in a direction oriented toward the distal end of the lead.

10. The assembly according to claim 9, wherein the second branch extends from the lead body from a second junction point of the lead body that is different from both the second portion and the first branch.

11. The assembly according to claim 10, wherein the second junction point of the second branch of the lead body is spaced apart by a distance of between 1 and 30 mm from the junction point of the first branch.

12. The assembly according to claim 10, wherein the lead body comprises at least one electrode arranged between the junction point of the first branch and the second junction point of the second branch.

13. The assembly according to claim 1, wherein the lead is a flexible microwire comprising an electrically conductive core coated with an electrically insulating layer.

14. The assembly according to claim 13, wherein at least one electrode is formed by a stripped zone of the microwire and a diameter of the microwire is no more than 1 French.

15. A flexible implantable stimulation lead, comprising:

a lead body comprising a proximal end and a distal end, wherein the lead is configured to be combined with an active implantable medical device via the proximal end of the lead and being configured to be implanted through a right ventricular free wall via the distal end of the lead, the lead comprising a first portion configured to be inserted into a needle of an assembly, the first portion comprising at least a first branch that extends from the lead body in a direction oriented toward the proximal end of the lead and toward a pointed free end of the needle when the first portion is inserted into the needle, wherein the first branch extending from the lead body is arranged in a predetermined distance from the distal end of the lead, the predetermined distance corresponding to a second portion of the lead body between the first branch and the distal end of the lead;

wherein the lead body further comprises a third portion that is less rigid than the first branch and the second portion, the third portion extending toward the proximal end of the lead from a junction point of the first branch, such that the first branch and the second portion are configured to pivot securely with one another relative to the junction point;

wherein, in a state where the first portion is inserted into a needle, the first branch and the second portion form an obtuse angle and the first branch and the third portion form an acute angle; and wherein the first branch, the second portion, and the third portion are formed of the lead body as a single, continuous piece, the third portion defining a bending zone of the lead distinct from the first portion.

16. The flexible implantable stimulation lead according to claim 15, wherein the first portion of the lead further comprises a bearing formed by a second branch that extends from the lead body in a direction oriented toward the distal end of the lead.

17. The flexible implantable stimulation lead according to claim 16, wherein the second branch extends from the lead body from a second junction point of the lead body that is different both from said second portion and from the first branch.

18. The flexible implantable stimulation lead according to claim 15, wherein the lead body further comprises a third portion that is less rigid than the first branch and the second portion.

19. The flexible implantable stimulation lead according to claim 18, wherein the third portion extends toward the proximal end of the lead from a junction point of the first branch, such that the first branch and the second portion are configured to pivot securely with one another relative to the junction point of the first branch.

* * * * *